US010799423B2

(12) United States Patent
Sund et al.

(10) Patent No.: US 10,799,423 B2
(45) Date of Patent: *Oct. 13, 2020

(54) LIQUID-TRANSFER ADAPTER BEVELED SPIKE

(71) Applicant: FERRING INTERNATIONAL CENTER S.A., Saint-Prex, OT (CH)

(72) Inventors: Julius C. Sund, Plymouth, MN (US); Kevin D. Swanson, Plymouth, MN (US)

(73) Assignee: FERRING INTERNATIONAL CENTER S.A., Saint-Prex (CH)

( * ) Notice: Subject to any disclaimer, the term of this patent is extended or adjusted under 35 U.S.C. 154(b) by 177 days.

This patent is subject to a terminal disclaimer.

(21) Appl. No.: 15/783,392

(22) Filed: Oct. 13, 2017

(65) Prior Publication Data

US 2018/0036204 A1 Feb. 8, 2018

Related U.S. Application Data

(63) Continuation of application No. 14/414,305, filed as application No. PCT/US2013/050206 on Jul. 12, 2013, now Pat. No. 9,789,027.

(Continued)

(51) Int. Cl.
*A61J 1/20* (2006.01)
*A61J 1/14* (2006.01)
*A61M 5/20* (2006.01)

(52) U.S. Cl.
CPC .......... *A61J 1/2096* (2013.01); *A61J 1/1406* (2013.01); *A61J 1/201* (2015.05); *A61J 1/2044* (2015.05);

(Continued)

(58) Field of Classification Search
CPC ........ A61J 1/2096; A61J 1/1406; A61J 1/201; A61J 1/2044; A61J 1/2055; A61J 1/2065; A61M 5/2033

(Continued)

(56) References Cited

U.S. PATENT DOCUMENTS 5,893,397 A 4/1999 Peterson et al.
7,029,458 B2 4/2006 Spohn et al.
(Continued)

FOREIGN PATENT DOCUMENTS

EP 2308452 A1 4/2011
JP H09290012 11/1997
(Continued)

OTHER PUBLICATIONS

Office Action dated Feb. 23, 2017 for Japanese Patent Application No. 2015-521829, 4 pages.

(Continued)

*Primary Examiner* — Philip R Wiest
(74) *Attorney, Agent, or Firm* — Morgan, Lewis & Bockius LLP

(57) ABSTRACT

A liquid-transfer adapter operatively interposable between an injector and a vial is provided. The liquid-transfer has an injector engaging portion configured for fluidly coupling to an injector and a vial coupling. The vial coupling includes a spike that has a spike axis and a tip portion configured for piercing a septum of a vial. The tip portion includes a plurality of facets that meet each other at one or more edges and at least one of the one or more edges is sloped with respect to the spike axis. The spike defines a channel extending therethrough in fluid communication with the injector engaging portion. A channel opening is defined in at least one of the facets and disposed without interrupting the edges.

21 Claims, 16 Drawing Sheets

Related U.S. Application Data

(60) Provisional application No. 61/671,037, filed on Jul. 12, 2012.

(52) U.S. Cl.
CPC ............ *A61J 1/2055* (2015.05); *A61J 1/2065* (2015.05); *A61M 5/2033* (2013.01)

(58) Field of Classification Search
USPC .................................................. 604/403–411
See application file for complete search history.

(56) References Cited

U.S. PATENT DOCUMENTS

| | | | | |
|---|---|---|---|---|
| 9,220,660 | B2* | 12/2015 | Sund | A61M 5/30 |
| 9,789,027 | B2* | 10/2017 | Sund | A61J 1/2096 |
| 2003/0229330 | A1* | 12/2003 | Hickle | A61M 5/142 |
| | | | | 604/411 |
| 2004/0236305 | A1* | 11/2004 | Jansen | A61J 1/2096 |
| | | | | 604/411 |
| 2006/0025747 | A1* | 2/2006 | Sullivan | A61J 1/2096 |
| | | | | 604/411 |
| 2006/0200095 | A1* | 9/2006 | Steube | A61J 1/2096 |
| | | | | 604/272 |
| 2006/0229572 | A1* | 10/2006 | Lopez | A61J 1/20 |
| | | | | 604/256 |
| 2008/0185069 | A1 | 8/2008 | Clark | |
| 2009/0326485 | A1* | 12/2009 | Carlyon | A61J 1/2096 |
| | | | | 604/272 |
| 2013/0303994 | A1* | 11/2013 | Gaillot | A61J 1/2096 |
| | | | | 604/239 |

FOREIGN PATENT DOCUMENTS

| | | |
|---|---|---|
| JP | 2005516696 | 6/2005 |
| JP | 2007-275441 A | 10/2007 |
| JP | 2010538744 | 12/2010 |
| WO | 200152920 A2 | 7/2001 |
| WO | 03066152 | 8/2003 |
| WO | 2005032623 | 4/2005 |
| WO | 2009038860 | 3/2009 |
| WO | 2010119392 A1 | 10/2010 |
| WO | 2011058545 A1 | 5/2011 |
| WO | 2013066435 A2 | 5/2013 |
| WO | 2014011958 A1 | 1/2014 |

OTHER PUBLICATIONS

English Translation for Office Action dated Feb. 23, 2017 for Japanese Patent Application No. 2015-521829, 4 pages.
Office Action dated Dec. 2, 2016 for Canadian Patent Application No. 2,878,847, 5 pages.
English Translation of Second Office Action dated Mar. 1, 2017 for Chinese Patent Application No. 201380037040.7, 10 pages.
Second Office Action dated Mar. 1, 2017 for Chinese Patent Application No. 201380037040.7, 8 pages.
Extended European Search Report for European Patent Application No. 13817419.8 dated Dec. 8, 2015.
Japanese Office Action dated Aug. 1, 2019 for Japanese Patent Application No. 2018/167548, 11 pages.

* cited by examiner

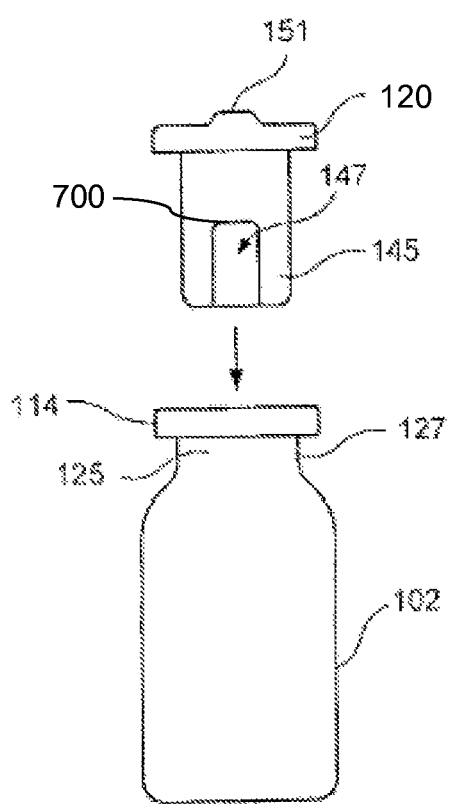
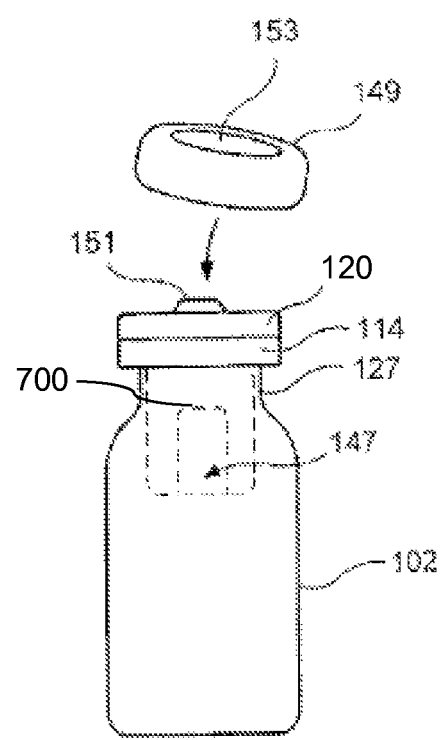
FIG. 4
FIG. 5

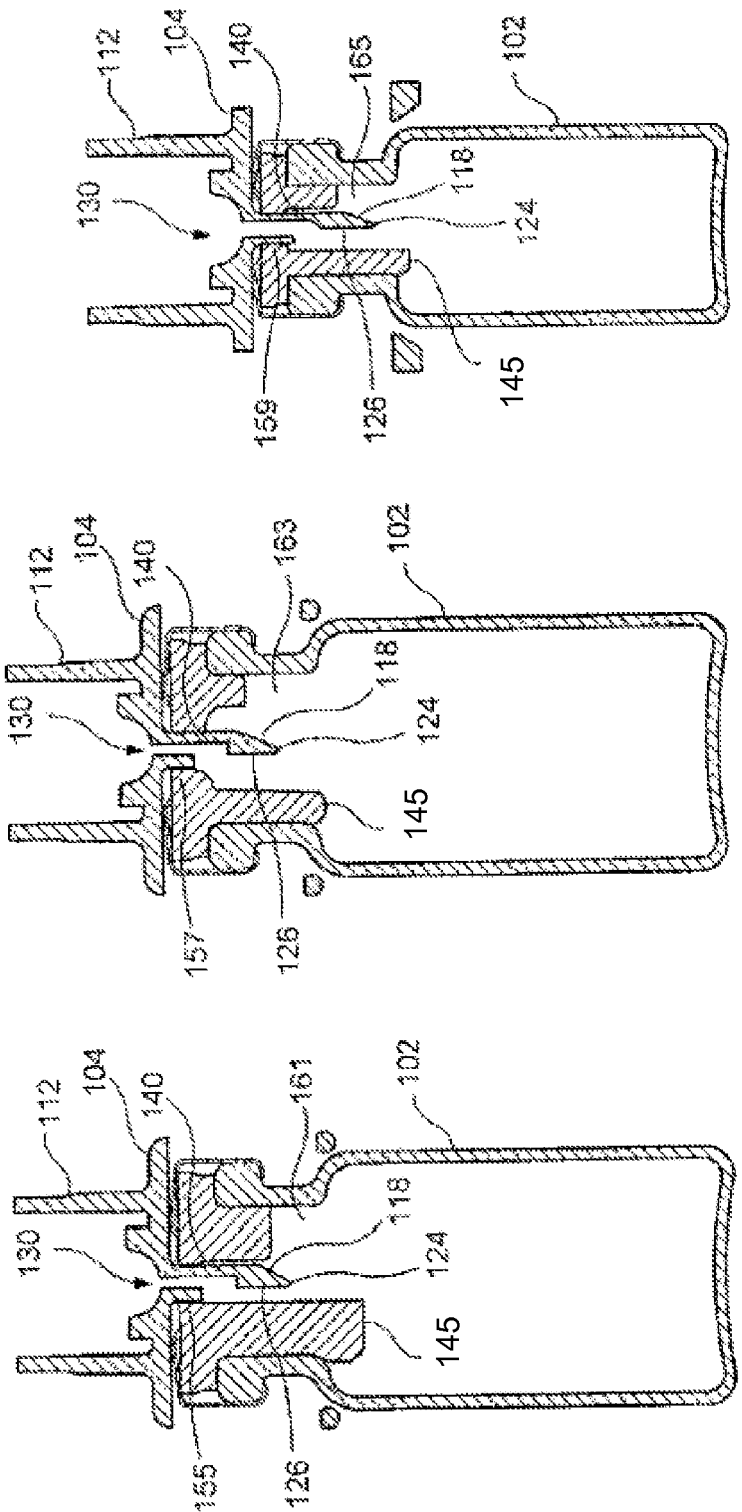

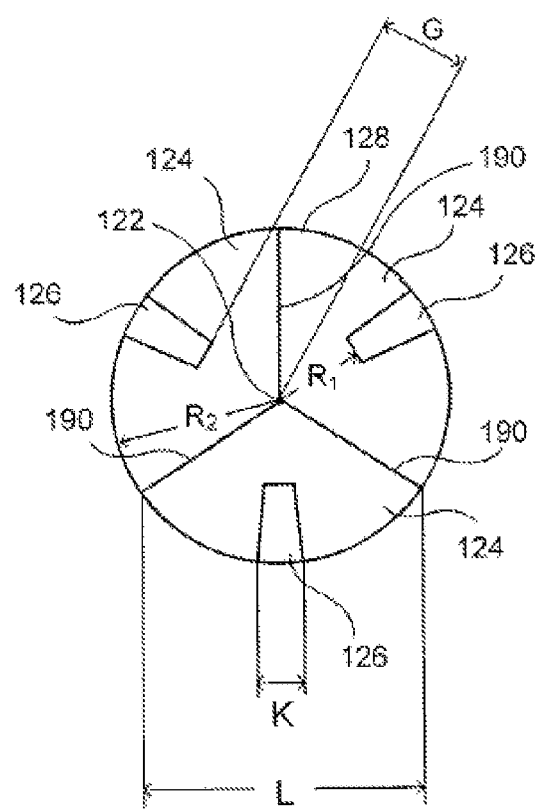
F I G. 11

LIQUID-TRANSFER ADAPTER BEVELED SPIKE

CROSS-REFERENCE TO RELATED APPLICATIONS

This application is a continuation of U.S. patent application Ser. No. 14/414,305 filed Jan. 12, 2015, which is a National Stage Patent Application of International Application No. PCT/US2013/050206, filed 12 Jul. 2013, which claims benefit from U.S. Provisional Patent Application No. 61/671,037, filed 12 Jul. 2012, each of which is incorporated by reference herein in its entirety.

TECHNICAL FIELD

The present application relate generally to liquid-transfer adapters and, more specifically, to liquid-transfer adapters that provide liquid communication between vials and injectors.

BACKGROUND

In the medical field, it is common practice for medication to be provided in a vial. The medication is transferred from the vial to an injector (e.g., a syringe, auto-injector, jet injector, and so forth) for subsequent injection into a patient. In some cases, the medication is provided in a liquid solution in the sealed vial, while in other cases it is provided in a solid form (e.g., powder). Generally, when provided in solid form, a solvent (e.g., water) is inserted into the vial to dissolve the medication. The liquid medication is extracted out of the vial into an injector for injection into a patient.

A typical vial is sealed with a stopper that can have sidewalk extending down the inside walls of a neck portion of the vial. The side wall geometry and thickness can vary depending on the nature of the drug including but not limited to drugs which are in powder form that require a solvent for dissolution. Conventionally, a hollow spike is been implemented to provide fluid communication with the contents of the vial. In particular, the hollow spike punctures the stopper to insert and/or extract liquid from the vial. Occasionally, however, when attempting to puncture the stopper, the Spike 118 may inadvertently enter into a sidewall of the stopper, preventing or limiting liquid communication with the contents of the vials, depending on the orientation of the opening to draw the fluid from the vial into the spike.

Additionally, as conventional spikes are pushed through rubber stoppers, the rubber stoppers are often stretched, torn, or cut by the spike. In some cases portions of the stopper may enter into the hollow spike and may even core the stopper resulting in obstruction of liquid flow from the vial.

U.S. Pat No. 5,254,106 discloses a needle that includes a slot that extends along the sidewalls of the needle. Similarly, U.S. Pat. Pub. No. 2006/0266431 discloses a needle with slots in the sidewall. U.S. Pat. No. 4,411,661 and U.S. Pat. Pub. No. 2007/0179506 disclose a spike with a slot that extends from a conical tip on its sidewalk. U.S. Pat. No. 7,150,735 discloses a spike with one or more openings in a beveled surface. All of these patent documents are incorporated by reference herein in their entirety.

SUMMARY

A liquid-transfer adapter operatively interposable between an injector and a vial is provided. In some embodiments, the liquid-transfer adapter has an injector engaging portion configured for fluidly coupling to an injector and a vial coupling. The vial coupling includes a spike that has a spike axis and a tip portion configured for piercing a septum of a vial. The tip portion includes a plurality of facets that meet each other at one or more edges and at least one of the one or more edges is sloped with respect to the spike axis. The spike defines a channel extending therethrough in fluid communication with the injector engaging portion. A channel opening is defined in at least one of the facets and disposed without interrupting the edges 190.

In some embodiments, the edges comprise junctions between the facets. The edges may also have cutting surfaces configured for cutting the septum as the spike 118 is pushed therethrough. In one embodiment, the tip portion has at least three facets and the channel opening comprises a channel opening disposed in each of at least three of the facets. The channel openings may be spaced circumferentially from the edges 190. Additionally, lateral edges of the channel openings may be disposed radially inward compared to the edges 190. Moreover, lateral edges of the channel openings are disposed radially inward relative to the edges at any axial position. The lateral edges of the channel openings may be spaced from the edges sufficiently to minimize intrusion of the septum into the channel openings when the spike 118 is pierced through the septum. The channel openings may be substantially centered circumferentially on the facets.

In some embodiments, a seal may be disposed at the injector engaging portion configured for mating with the injector for maintaining liquid within the channel and injector. Additionally, the injector engaging portion has dimensions suitable for coupling with a needle free injector. Moreover, a removable insert may be removably coupled within the injector engaging portion for selectively configuring the injector engaging portion for engaging variously sized injectors. The removable insert may have dimensions suitable for coupling with a syringe having a first width, and with the insert removed, the injector engaging portion is configured for coupling to a jet injector having a second width that is larger than the first width.

In some embodiments, a vial engaging member may be associated with the vial coupling portion and configured for engaging the liquid-transfer adapter 104 to the vial with spike inserted therein. Moreover, the vial engaging member may include reflexed fingers arranged around the spike and extending theretowards for snapping to and retaining the liquid-transfer adapter 104 engaged to the vial. Further, the Spike 118 may include a shaft extending from the tip towards the injector engaging portion and an opening extends onto the shaft for maximizing fluid extraction from the vial with the vial in an inverted position.

In some embodiments, the edges meet at a point that is substantially axially centered. Additionally, the facets may be substantially flat bevels. In still other embodiments, a liquid-transfer adapter 104 is provided having a spike for providing liquid communication to a sealed vial. The spike includes a shaft portion and a piercing point configured for piercing a septum of a vial. The tip includes at least three bevels joining together at a substantially centered tip, a channel extending through the spike, and a channel opening disposed within each bevel and onto the shaft portion. The channel openings are connected to the channel for transferring fluid to or from the vial.

In some embodiments, the invention includes a liquid-transfer adapter 104 operatively interposable between an injector and a vial, the liquid-transfer adapter 104 including an injector engaging portion configured for fluidly coupling to an injector; a vial coupling including a spike that has a spike axis and a tip portion configured for piercing a septum of a vial, the tip portion including plurality of facets that meet each other at one or more edges, at least one of the one or more edges being sloped with respect to the spike axis, the spike defining a channel extending therethrough in fluid communication with the injector engaging portion and including a channel opening defined in at least one of the facets and disposed without interrupting the edges, and, a collar associated with the vial coupling configured to act as guide for engaging the liquid-transfer adapter 104 to the vial with the spike inserted therein.

BRIEF DESCRIPTION OF THE DRAWINGS

The drawings depict one or more implementations in accordance with the present concepts, by way of example only, not by way of limitation. In the drawings, like reference numerals refer to the same or similar elements.

FIGS. 4-5 illustrate the vial before and after being sealed with a stopper 120, respectively;

FIGS. 6-8 are cross-sectional views of various adapter configurations to connect to various sizes of vials for liquid-transfer;

FIG. 11 is an axial view of the liquid-transfer of FIG. 9 from a vial coupling end;

DETAILED DESCRIPTION

Figure 1:
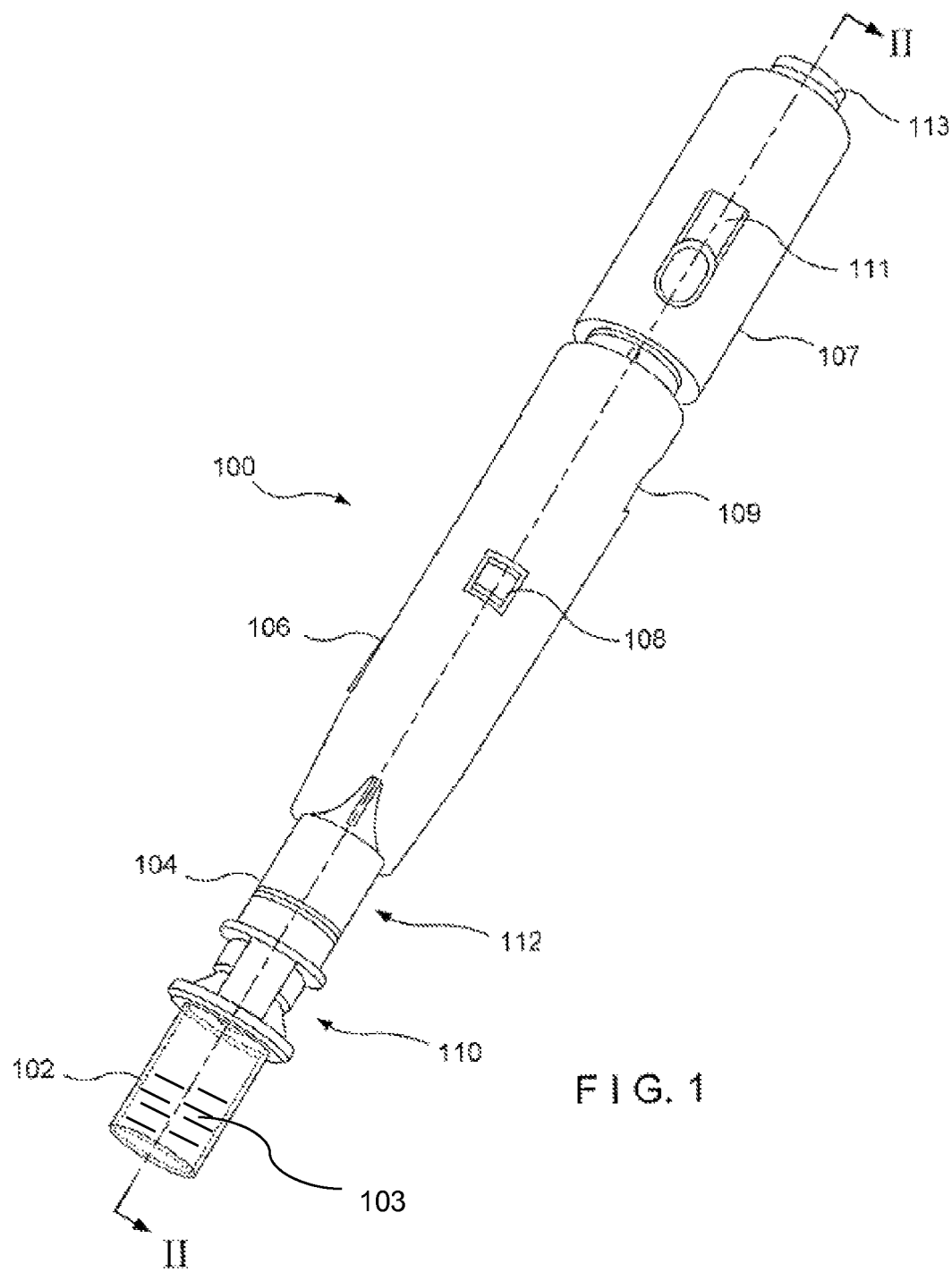
FIG. 1 shows a liquid-transfer system in accordance with an example embodiment.

Referring to FIG. 1, a liquid-transfer system 100 is illustrated in accordance with an example embodiment. In one embodiment, the liquid-transfer system 100 includes a vial 102 holding liquid 103, a liquid-transfer adapter 104 and an injector 106. In another embodiment, the liquid-transfer adapter 104 provides liquid communication between the vial 102 and the injector 106 to facilitate the transfer of liquid to and/or from the vial 102, and to and/or from the injector 106.

The injector 106 may have an indicator window 108 for indicating a volume of liquid 103 that it contains (e.g., the amount of liquid retrieved from the vial 102). The injector 106 may take one of several different forms, including a syringe, an auto injector, or a jet injector (needle free or needle-assisted). Information regarding injectors may be found in U.S. Pat. No. 5,875,976, and/or 6,673,035, which are incorporated by reference herein in their entirety and for all purposes. It should be appreciated that the needle-free injectors described in these references can be adapted for needle-assisted injection, auto injection, and/or other types of injection.

The liquid-transfer adapter 104 can be operatively coupled in between the vial 102 and the injector 106. The liquid-transfer adapter 104 has a vial engaging end 110 that receives the vial 102 and couples the vial with the liquid-transfer adapter 104. Additionally, the liquid-transfer adapter 104 has an injector engaging end 112 to which the injector 106 can be attached.

Figure 2:
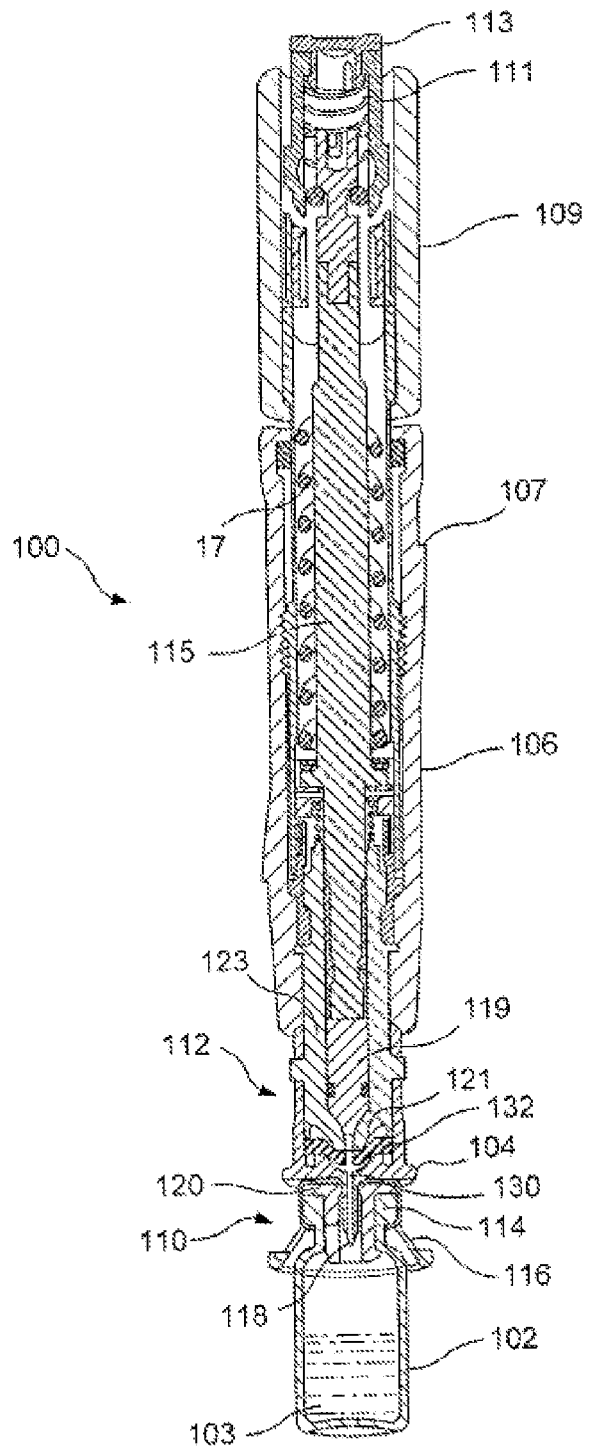
FIG. 2 is a cross-sectional view of the liquid-transfer system of FIG. 1 taken along line II-II.

FIG. 2 is a cross-sectional view of the liquid-transfer system of FIG. 1 taken along line II-II. As shown, the injector 106 includes a distal housing 107 and a proximal housing 109. The proximal housing 109 includes a trigger mechanism 111 and a button 113 for firing the injector 106. The distal housing 107 includes a ram 115 and an energy source 17 (e.g., a firing spring) associated therewith to provide energy for firing the injector 106. A firing stopper 119 may be attached to the distal end of the ram 115 to force out fluid medicament through a jet nozzle 121 when the injector 106 is fired. Additionally, the firing stopper 119 moves proximally to draw liquid 103 from the vial 102 into a cartridge 123. A seal 132 interfaces the jet nozzle 121 of the cartridge 123 and is generally located between the liquid-transfer adapter 104 and the distal end of the injector 106. The seal 132 may maintain liquid within the channel 130 and an injector 106 coupled to the liquid-transfer adapter 104.

Figure 3:
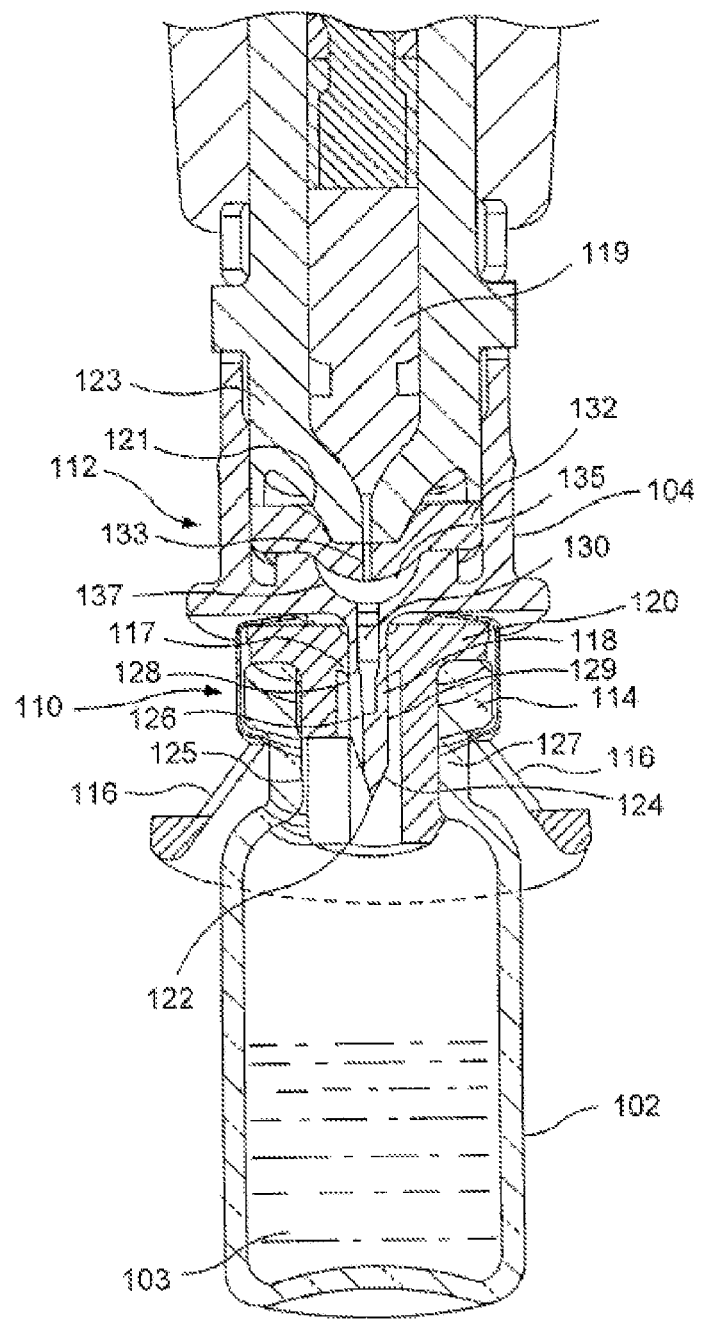
FIG. 3 is a cross-section view of a distal portion of the distal end of the liquid-transfer of FIG. 2 coupled to a vial.

FIG. 3 is an enlarged view of a portion of FIG. 2 showing the vial 102 and the liquid-transfer adapter 104. In one embodiment, the vial 102 has a neck 125 and a lip 114 that protrudes radially beyond a recessed portion of the neck 127 which may be used to engage the vial 102 with the liquid-transfer adapter 104. Fingers 116 of the liquid-transfer adapter 104 can be provided to seat on and engage the lip 114 to hold the vial 102 in an engaged position with respect to the liquid-transfer adapter 104. The fingers 116 may be arranged around the spike 118 and extending theretowards for snapping to and retaining the liquid-transfer adapter 104 engaged to the vial 102.

The engagement of the vial 102 with the liquid-transfer adapter 104 causes a spike 118 of the liquid-transfer adapter 104 to puncture a septum 700 (shown in FIG. 4) of the vial 102. In one embodiment, the spike 118 may be a multifaceted spike having a tip 122 that is axially centered with respect to the central axis of the spike 118. In such embodiments, the tip 122 can have a coaxial point, but in alternative embodiments, the tip and point can be provided off center. One or more facets 124 may include a channel opening 126. Some or all of the channel openings 126 extend on the facet 124 and onto the sidewall 128 of the shaft 129 of the spike 118. As the spike 118 is pushed through the septum 700, the septum is deformed (as shown at 117) as the sidewall 128 of the shaft 129 pulls on the septum. In one embodiment, the channel openings 126 extend down the sidewall 128 of the shaft 129 so that when the spike 118 is inserted through the septum 700 at least a portion of a channel opening 126 does not extend past septum 700, ensuring that any liquid that flows into a gap 147 has access to at least a portion of a channel opening 126. The channel openings 126 are fluidly connected to an interior channel 130 that extends longitudinally through the spike 118 thereof. The channel openings 126 are generally spaced circumferentially from the edges 190 (FIG. 11). Further, the lateral edges of the channel openings 126 are radially positioned inwardly from the edges 190 at any axial station. The channel 130 provides liquid communication between the vial engaging end 110 and the injector engaging end 112 of the liquid-transfer adapter 104.

FIGS. 2 and 3 also show a seal 132, such as a rubber seal or elastomeric septum, which is positioned within the injector engaging end 112 over a terminal end of the channel 130 and configured to prevent fluid from leaking from the interface between the injector engaging end 112 and the injector 106 that is coupled therewith. The seal 132 includes an opening 133 to fluidly communicate the channel 130 to the injector 106. The seal 132 includes a domed region 135 that corresponds with a dome cutaway 137 in the liquid-transfer adapter 104 and which helps to achieve a seal. In one embodiment, the jet nozzle 121 slightly deforms the seal 132 when the two are interfaced.

FIG. 4 illustrates the vial 102 before it is sealed with the stopper 120. The vial 102 has the recessed neck portion 127 and the lip 114. Medicament may be inserted into the vial 102 prior to placing the stopper within the neck 125 of the vial. The stopper 120 may include a stopper sidewall 145 that is configured to extend into the neck 125 of the vial. Before sealing the vial 102, the stopper 120 may be partially inserted into the vial 102 and forming a gap 147 of the stopper sidewall 145. The gap 147 may take the form of a shortened portion of the stopper sidewall 145 or a hollowed portion of stopper 120. The medicament may be placed in the vial in a liquid or a solid form. Additionally, in some embodiments, a liquid medicament inserted into the vial 102 may be heated or otherwise treated so as to be solid before fully inserting the stopper 120. As shown in FIG. 5, once the stopper 120 is fully inserted into the vial 102, a cap 149 (e.g., a metal cap) is positioned over the stopper 120 and cap 149 may subsequently be crimped about the lip 114 of the vial 102 to secure the stopper 120 and seal the vial. The cap 149 may have a removable tab 153 that may be removed for insertion of a spike, such as the spike 118 of the liquid-transfer adapter 104. The stopper 120 may have a circular protrusion 151 on its top that may serve to provide a target for the spike. The removable tab 153 may be generally centered over this protrusion 151 in some embodiments so that when it is removed the protrusion 151 is exposed. It should be appreciated that the stopper 120 and/or vial 102 may be provided in a variety of different sizes and/or dimensions.

FIGS. 6-8 and 10 show the cross-sectional views of the liquid-transfer adapter 104 with the vial 102 with exemplary stoppers each having different dimensions, Specifically, FIG. 6 illustrates a 20 mm diameter vial lip stopper 155, FIG. 7 illustrates an alternate 20 mm diameter vial lip stopper 157, and FIG. 8 illustrates a 13 mm diameter vial lip stopper 159. Each of the stoppers 155, 157 and 159 has a gap 161, 163, and 165, respectively. The spike 118 can have the same dimensions in the liquid-transfer adapters sized for use with different vials, such as in each of the adapters in FIGS. 6-8. A common mold may be used for the spike 118 that is functional in a variety of adapters and with a variety of vial and stopper sizes. As such, molds for the other parts of the liquid-transfer adapter 104 may vary but only a single mold need be designed and prepared for the spike 118 in this embodiment, thus providing manufacturing efficiency and savings.

As may be seen in FIGS. 6-8, in one embodiment, channel openings 126 of the spike 118 extend onto or along the spike sidewall 128 from the facets 124 to a distance from the tip that is sufficient so that a portion of the channel openings 126 extends past septum 700 (not shown). In some embodiments, at least a portion of channel openings 126 is retained in stopper 155, 157 or 159 and a portion of channel openings 126 extends into a gap of the stopper (e.g., gaps 161, 163 and 165). In another embodiment, at least a portion of channel openings 126 is flush with septum 700. In another embodiment, a proximal portion of channel openings 126 does not completely extend into a gap and past septum 700. It should be appreciated, that there may be some deformation of the center portions stoppers (e.g., stoppers 155, 157, 159) when the spike 118 is pushed through, as shown in FIG. 3 at 117. The deformation is not shown in FIG. 6-8. However, generally, the channel openings 126 of the spike 118 terminates at some point within the center portions of the septums so that when the coupled vial, liquid-transfer adapter 104, and injector are inverted with the vial on top, the amount of fluid that can be withdrawn from the vial is maximized compared to having the channel openings 126 terminate outside of the stopper sidewall 145. In an alternative embodiment, however, some or all of the channel openings 126 can be shorter so as to remain spaced from the stopper sidewall 145 when the spike 118 is fully inserted therein.

Referring again to 4 and 5, it should be appreciated that the extent to which a portion of the channel openings 126 remains within or in contact with or sealingly engaged with the stopper 120 and/or the extent to which the end 140 of the channel openings 126 extends beyond the septum 700 may depend on several factors such as the thickness of the stopper 120, the length of the channel and/or the extent to which the channels extend down the sidewall of the spike. It should be appreciated, however, that, in certain embodiments, the dimensions of the spike 118 are such that they function as intended for a variety of different dimensioned septums/stoppers and/or vials. As such, the tooling for the spike 118 can be reused. The liquid-transfer adapter 104 dimensions may vary to accommodate the different sizes of vial necks, for instance. In other embodiments, the dimensions of the Spike 118 may vary and tooling may be created to accommodate various spike sizing/dimensions.

Figure 9:
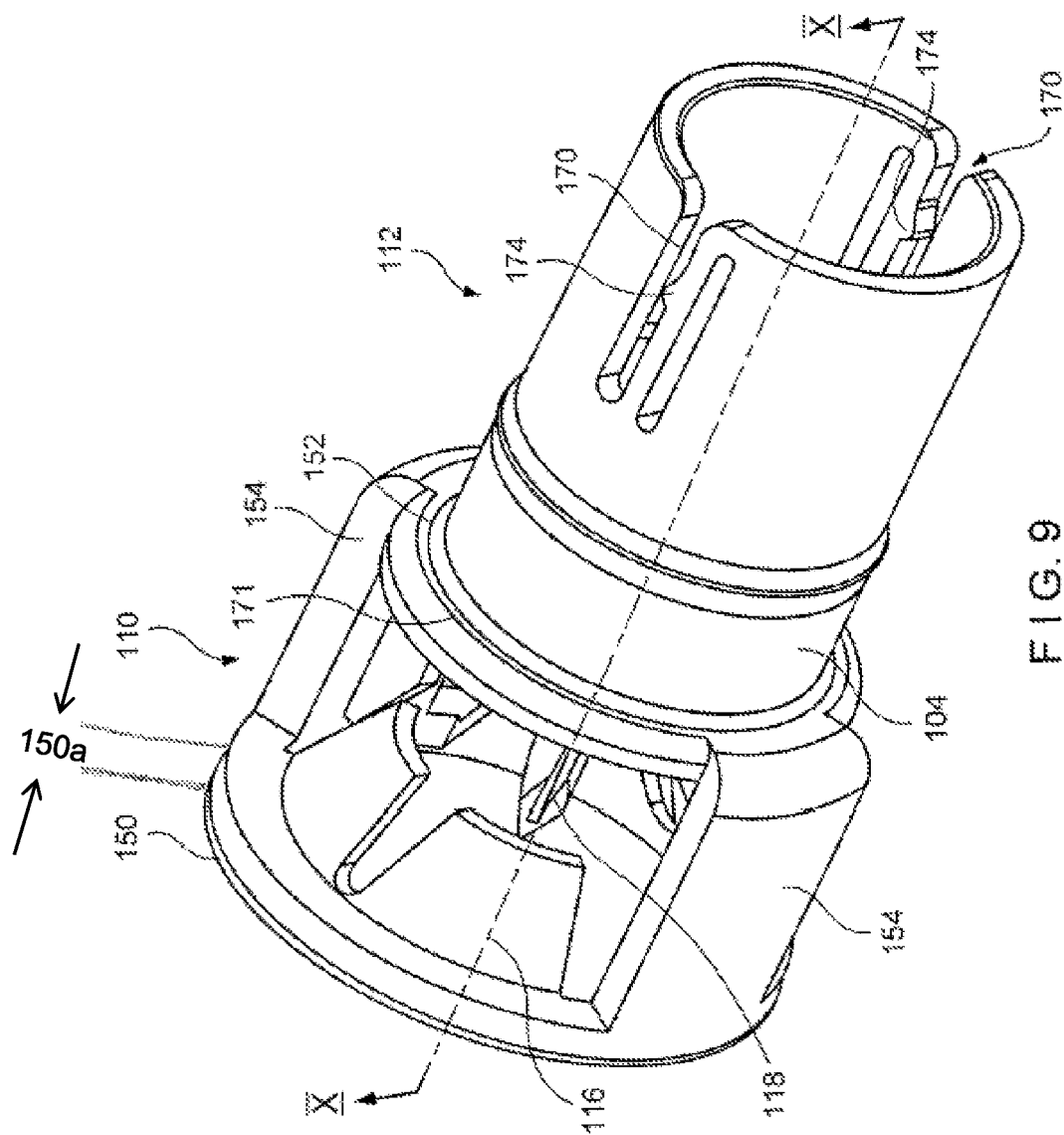
FIG. 9 is a perspective view of the liquid-transfer adapter of FIG. 1.
Figure 22:
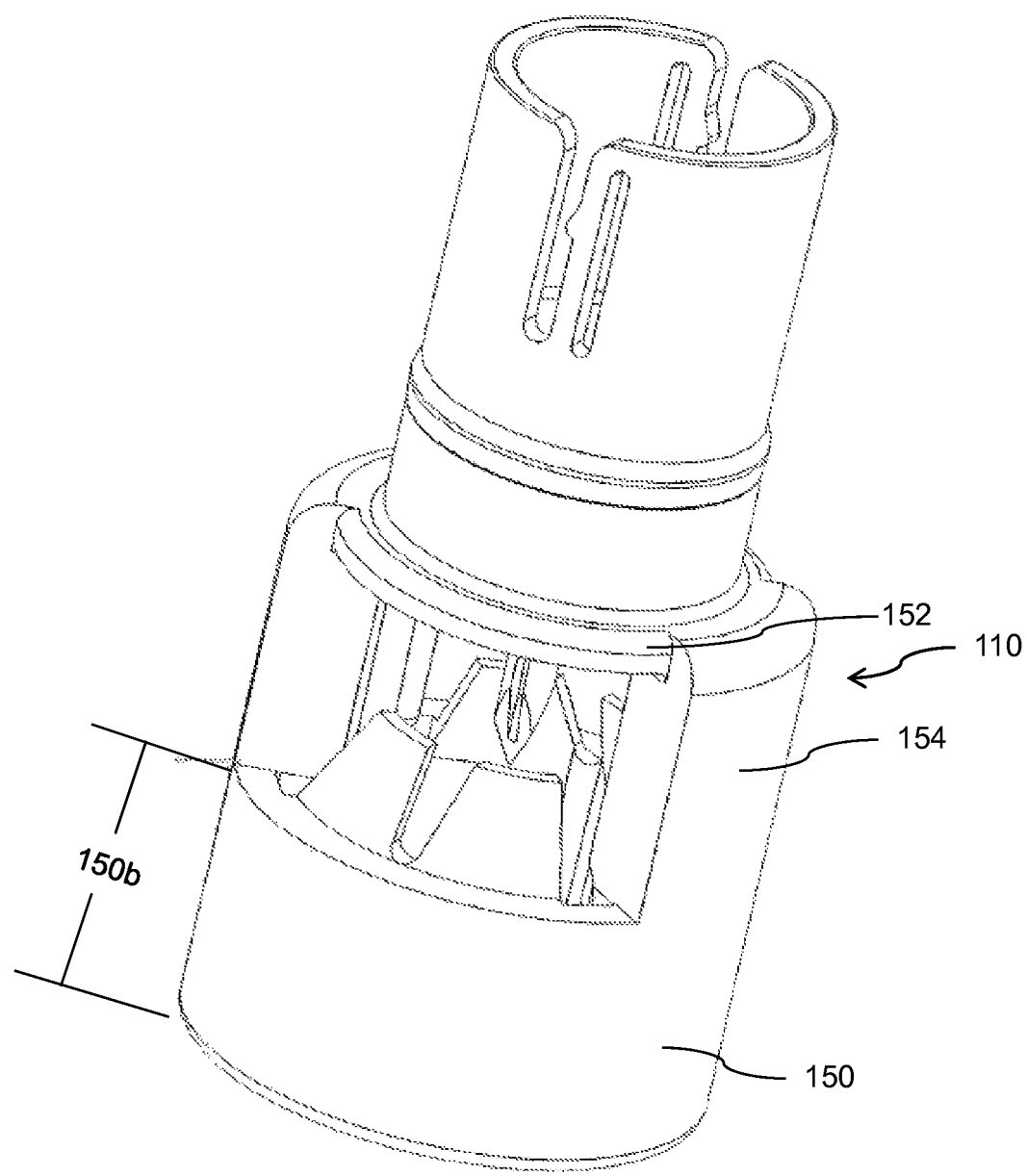
FIG. 22 is a perspective view of an exemplary embodiment of a liquid-transfer adapter 104.

FIG. 9 is a perspective view of the liquid-transfer adapter 104 without a vial. The vial engaging end 110 includes a collar 150 that couples to a center body 152 of the liquid-transfer adapter 104 with support structures 154. Collar 150 can have varied height. For example, in one embodiment, collar 150 has height 150a as shown in FIG. 9. In another embodiment, collar 150 has height 150b as shown in FIG. 22. In one embodiment, collar 150 height is about 0.05 inches, about 0.10 inches, about 0.15 inches, about 0.2 inches, about 0.25 inches, about 0.3 inches, about 0.35 inches, about 0.4 inches, about 0.45 inches, about 0.50 inches, about 0.55 inches, about 0.6 inches, about 0.65 inches, about 0.70 inches, about 0.75 inches, about 0.80 inches, about 0.85 inches, about 0.90 inches, about 0.95 inches, about 1.00 inches, or any range determinable from the preceding dosage amounts (for example, about 0.10 inches to about 1 inch or about 0.45 inches to about 0.60 inches). In one embodiment, the height of collar 150 is about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 85%, about 190%, about 195%, about 200%, about 205%, about 210%, about 215%, about 220%, about 225%, about 230%, about 235%, about 240%, about 245%, about 250%, about 255%, about 260%, about 265%, about 270%, about 275%, about 280%, about 285%, about 290%, about 295%, about 300% or any range determinable from the preceding percentages (for example, about 1% to about 100% or about 55% to about 115%) of the height of support structures 154. In one embodiment, collar 150 is configured to act as guide for the liquid-transfer adapter 104 as the vial 102 engaging end 110 engages a vial 102. In one embodiment, the collar 150 is of sufficient dimension to allow a user to approach a vial 102 with the liquid-transfer adapter 104 at various angles relative to the stopper 120 of the vial 102 without impeding fluid introduction into the vial 102 or withdrawal of fluid from the vial 102. In one embodiment, the collar 150 aligns the spike 118 with a pierceable surface of a stopper 120 prior to the spike coming into contact with the pierceable surface of the stopper 120. In one embodiment, the collar 150 is of sufficient dimension (e.g., height, circumference, thickness) to predispose insertion of the spike 118 in the vial 102 septum to substantially avoid the stopper 120 sidewall 145. In another embodiment, the collar 150 is of sufficient dimension to allow an attachment to a vial 102 with the liquid-transfer adapter 104 at angles relative to the stopper 120 of the vial 102 without impeding fluid introduction into the vial 102 or withdrawal of fluid from the vial 102. In one embodiment, collar 150 is generally cylindrical. Though, collar 150 is not limited to such shape and may be any suitable regular or irregular shape. In one embodiment, the center body 152 includes a wall 171 that divides the vial 102 and injector engaging ends 110 and 112 from each other, and the spike 118 extends from the center body 152. The collar 150 is held by the support structures 154 at a distance from the center body 152 greater than the length of the spike 118. In one embodiment, the height of support structure 154 is about 0.2 inches, about 0.25 inches, about 0.3 inches, about 0.35 inches, about 0.4 inches, about 0.45 inches, about 0.50 inches, about 0.55 inches, about 0.6 inches, about 0.65 inches, about 0.70 inches, about 0.75 inches, about 0.80 inches, about 0.85 inches, about 0.90 inches, about 0.95 inches, about 1.00 inches, or any range determinable from the preceding heights (for example, about 0.30 inches to about 1 inch or about 0.45 inches to about 0.60 inches). Fingers 116 are distributed about the collar 150 and extend inwardly from the collar 150 towards the spike 118. The fingers 116 may be reflexed so as to snap to the vial 102 and retain the liquid-transfer adapter 104 engaged to the vial 102. Other embodiments may use different mechanisms to engage the liquid-transfer adapter 104 to the vial 102.

Engagement slots 170 on the injector engaging end 112 having engagement members 174 are also shown in FIG. 9. Generally, the engagement slots 170 may be configured to releasably receive and engage flanges of an injector or cartridge. Engagement members 174 may generally be resilient protrusions into the slots 170 configured to hold the flanges and the injector or cartridge in a coupled position relative to the liquid-transfer adapter 104.

With reference to FIG. 9, while particular dimensions of the liquid-transfer adapter 104 may vary, some example dimensions are provided herein to give a sense of the scale for certain embodiments of a liquid-transfer adapter 104. For example, the distance from an outer edge of the collar 150 to the end 112 of the fingers 116 may be, for example, up to around a half of an inch. In another embodiment, the distance from an outer edge of the collar 150 to the end of fingers 116 is between about 0.1-0.4 inches. In another embodiment, the distance from an outer edge of the collar 150 to the end 112 of fingers 116 is about a quarter inch. A plurality of fingers 116 may be provided, such as four fingers 116 provided in pairs, and configured with a desired stiffness for coupling with the vial 102. A length of the injector engaging end 112 is typically between about half an inch to an inch or greater, and in one embodiment is approximately 0.8 inches. Additionally, the diameter of the injector engaging end 112 may be up to or greater than about one inch. In one embodiment, the diameter of the injector engaging end 112 is between 0.4-0.7 inches, for example about half an inch, and in one embodiment about 0.6 inches.

Figure 10:
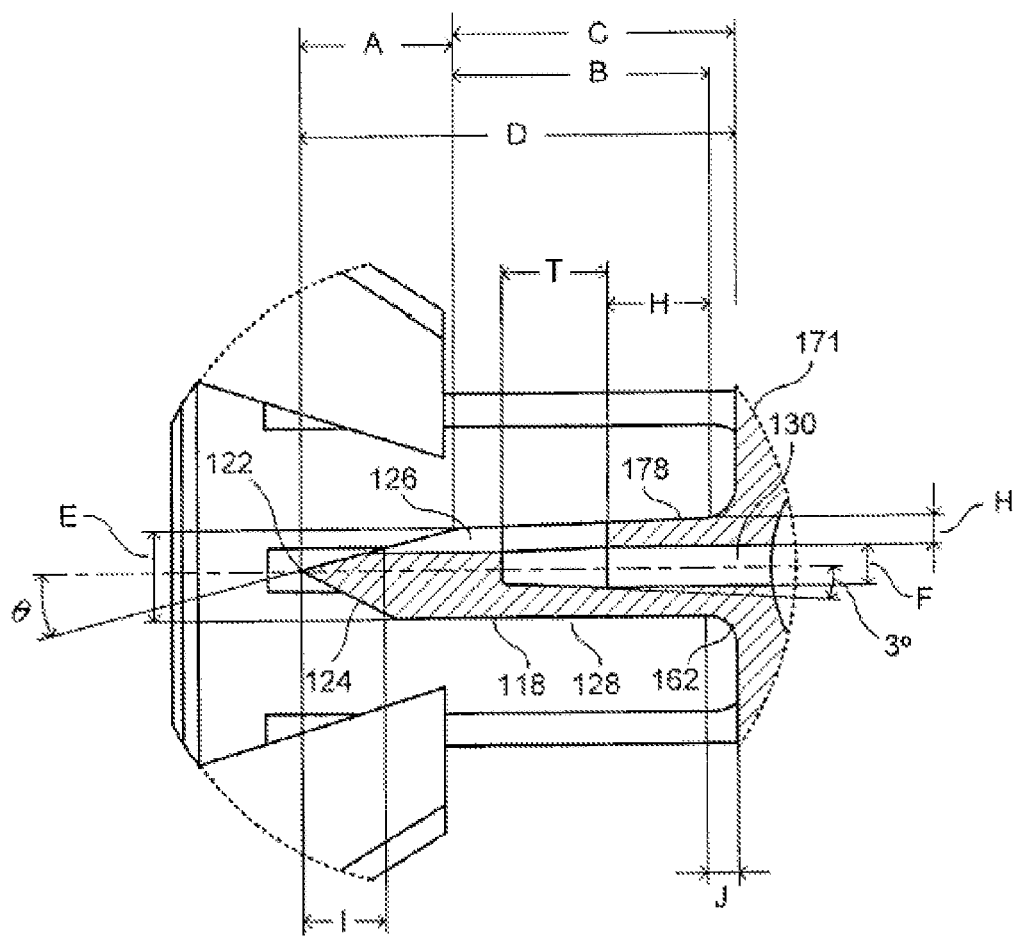
FIG. 10 is an enlarged cross-sectional of the liquid-transfer adapter of FIG. 9 taken along line X-X.

FIG. 10 is an enlarged cross-sectional view of the liquid-transfer adapter 104 of FIG. 9 taken along line X-X. The tip 122 of the spike 118 is shown as axially centered with the spike 118, although in other embodiments the Spike 118 may not be axially centered (e.g., may be offset from the center). Generally, the beveled facets 124 may have an angle θ relative to the axis of the spike 118 that is suitable for penetrating the vial stopper 120. For example, the angle θ may be up to about 45 degrees relative to the axis of the spike 118 and typically between about 10-20 degrees, or approximately 15 degrees in an embodiment. The beveled facets 124 may have a length A between 0.1-0.17 inches and in one embodiment 0.14 inches longitudinally along the spike 118. A length B along the shaft of the spike from the bevel to a curved portion of the base 162 may be between 0.21-0.29 inches and in one embodiment may be 0.24 inches. The curved portion of the base J may be between 0.01-0.03 inches and in one embodiment approximately 0.02 inches. A length C along the shaft of the spike 118 that includes the curved base 162 may be between 0.22-0.29 inches and may be 0.25 inches in one embodiment. As such, the ratios A/B and A/C may each be between approximately 1/3 to 3/4. In some embodiments, C may equal B+J.

The spike 118 may generally have a length D of up to or greater than about half of an inch or longer, and is, in one embodiment, between about 0.3 and 0.5 inches, and in another embodiment approximately 0.4 inches. The ratio of A/D may be between 1/5 to 2/3. The spike 118 may have a width E, typically, of about 0.05 to 0.2 inches, in one embodiment between 0.07-0.1 inches, and in another embodiment about 0.08 inches. The width E of the shaft may be slightly larger at a base 162 of the shaft 178. The channel 130 extends through the center of the spike 118 and may have a diameter F that may be between about 0.02-0.06 inches, and in one embodiment is about 0.04 or 0.05 inches and tapers proximally downward. The downward taper may begin where an overlap occurs between the channel 130 and the channel opening 126. The channel 130 may have a length between 0.1-0.2 inches from the base 162 of the shaft 178 to where the overlap occurs. The overlap of the channel and channel opening 126 may have a length T between 0.08-0.1 inches. The channel 130 may have a depth H between 0.02 and 0.03 inches, and in one embodiment may be approximately 0.025 inches. A ratio H/E may be between approximately 1/4 and 1/3. A longitudinal distance I from the tip 122 to the channel opening 126 may be between 0.06 and 0.08 inches, and in one embodiment may be 0.07 inches. A ratio A/I may be between approximately two and 3/4. In some embodiments, D may equal A+C or A+C+J.

FIG. 11 illustrates the spike tip 122 as having three facets or bevels that converge to a point 122. The facets 124 meet at edges 190 and channel openings 126 are located within the facets but do not interrupt the edges. The channel openings 126 may generally have a width K between 0.01-0.02 inches, and in one embodiment approximately 0.015 inches, while the facets 124 may generally each have an arcuate length L between edges of approximately 0.06 and 0.1 inches, and in one embodiment about 0.08 inches. A ratio of K/L may be between 1/10 and 1/3.

In one embodiment, the channel openings 126 are generally centered within the facets 124 so that they do not extend to the junctions of the facets. Thus, the lateral edges of the channel openings 126 are disposed radially inward compared to the edges 190 and are spaced. circumferentially from the edges. This is true at any axial station. As such a distance R1 measured from the axis to the channel openings 126 is less than a distance R2 from the axis to the peripheral end of edge 190. The channel openings 126 in this embodiment are about 120 degrees apart on center, seen in an axial direction, since they are about equally spaced and centered on the facets 124. The facets 124 may be spaced about the tip 122 of the spike 118 in any suitable manner. In some embodiments, the each facet 124 is the same size as the others, while in other embodiments one or more facets may be differently sized from the others. In an example, one or more facet 124 may have a width less than a tenth of an inch where it meets the sidewall 128 of the shaft. In one embodiment, the channel openings 126 may be up to about 30 degrees wide, measured on a radial plane, about the center and in one embodiment between 5-30 degrees wide (e.g., about 20 degrees wide in one embodiment). A distance G between the tip 122 and the channel openings 126 may be between 0.01-0.02 inches (e.g., 0.015 inches). In one embodiment, the channel openings 126 are tapered along the facets 124, but alternatively can have a substantially constant width.

It should be appreciated that the dimensions provided herein are merely exemplary and are not limiting. Indeed, in some embodiments the dimensions may be altered to accommodate certain functionality and/or to couple with injectors and/or vials having different dimensions.

Figure 12:
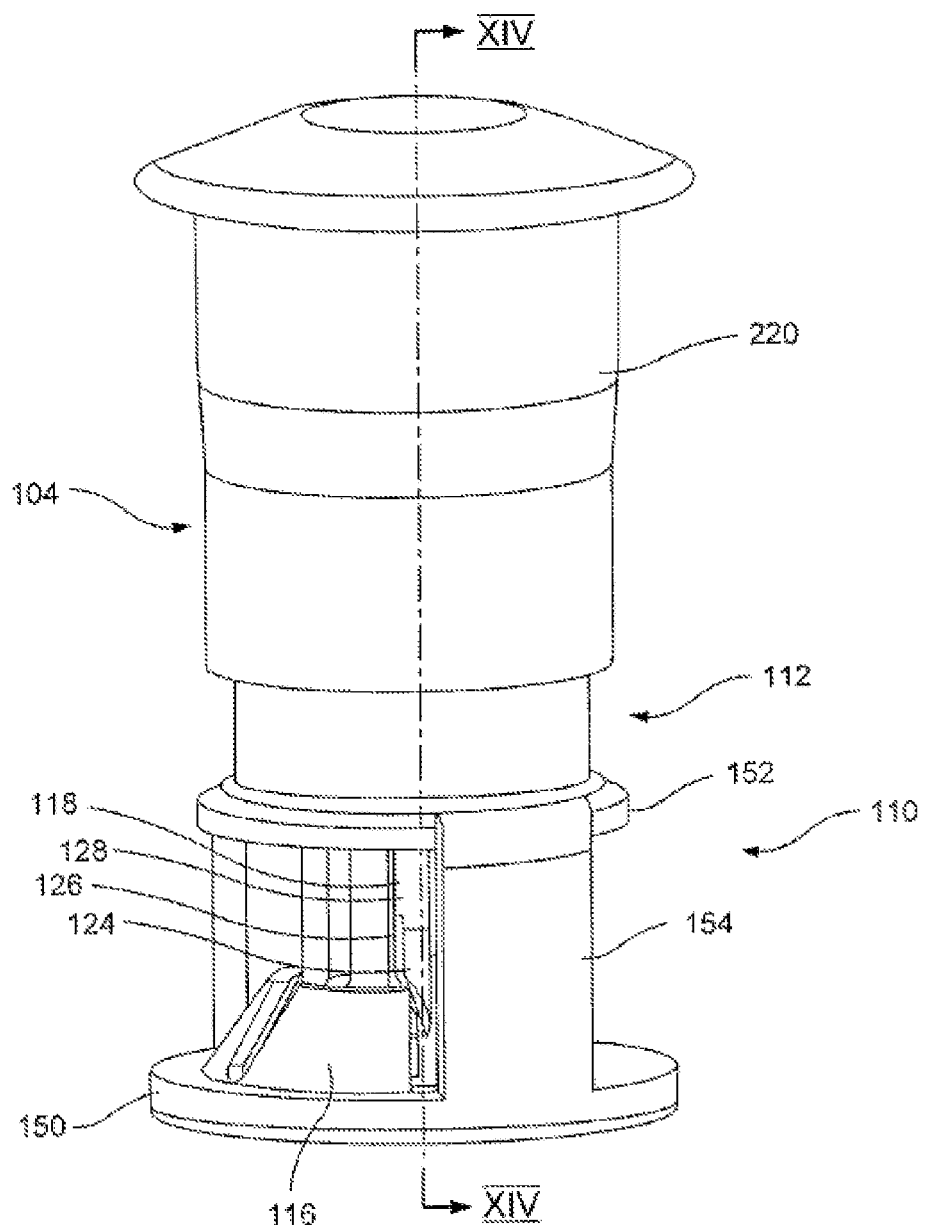
FIG. 12 illustrates a side view of the liquid-transfer of FIG. 1 having a cap prior to use of the adapter.

As illustrated in FIG. 12, a cap 220 can be provided that covers the injector engaging end 112 of the liquid-transfer adapter 104 prior to use to help keep the liquid-transfer clean. The cap 220 is removable to allow for coupling an injector with the liquid-transfer adapter 104.

Figure 13:
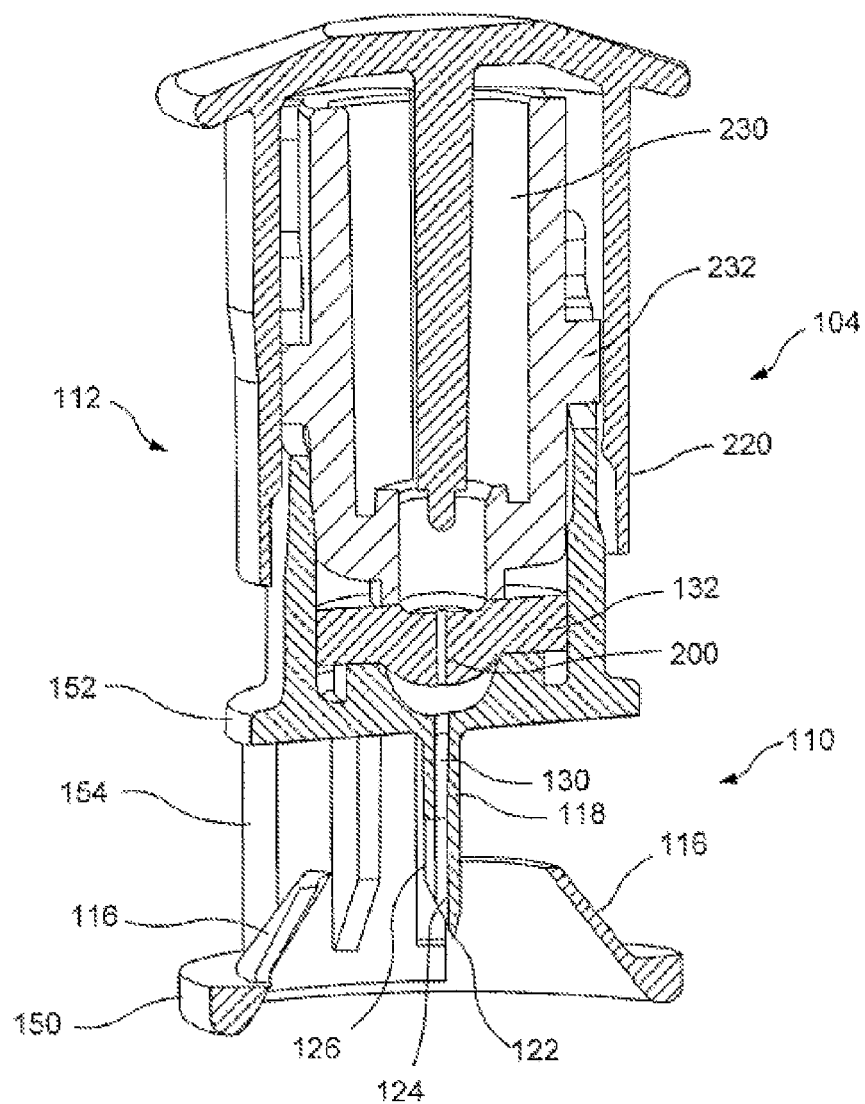
FIG. 13 is a cross-sectional view of the liquid-transfer shown in FIG. 12 taken along line XIV.

FIG. 13 is a cross sectional view taken along line XIV in FIG. 12. As illustrated, a removable insert 230 is positioned within the injector engaging end 112 of the liquid-transfer adapter 104. The insert 230 is configured to allow for injectors of differing sizes to be coupled and engaged to the liquid-transfer adapter 104. In some embodiments, for example, the interior dimensions of the injector engaging end 112 of the liquid-transfer adapter 104 may be configured to receive, and generally may correspond in size to, a preselected jet injector type. The insert 230 may be removed for use of the liquid-transfer adapter 104 with the jet injector. With the insert 230 in place, the insert can provide dimensions selected for receiving a syringe for reconstituting medicament. Generally, the insert 230 may include flanges 232 that may be inserted into engagement slots 170 of the liquid-transfer adapter 104 to secure the insert relative to the adapter. These same slots 170 may be used for engaging a jet injector in place as it is being loaded (e.g., as it extracts liquid from a vial).

Figure 14:
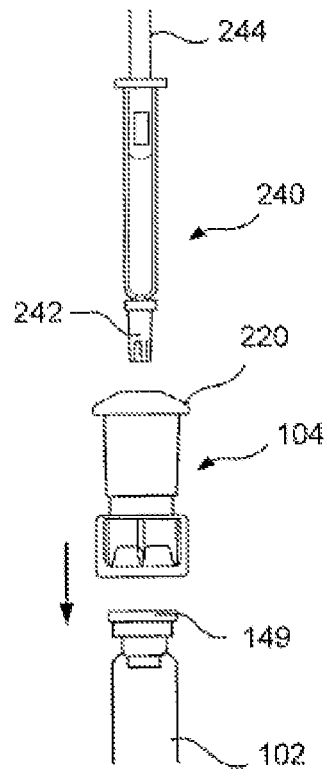
FIGS. 14-17 illustrate steps in an embodiment of a method of inserting liquid into the vial using the liquid-transfer and a removable insert.
Figure 15:
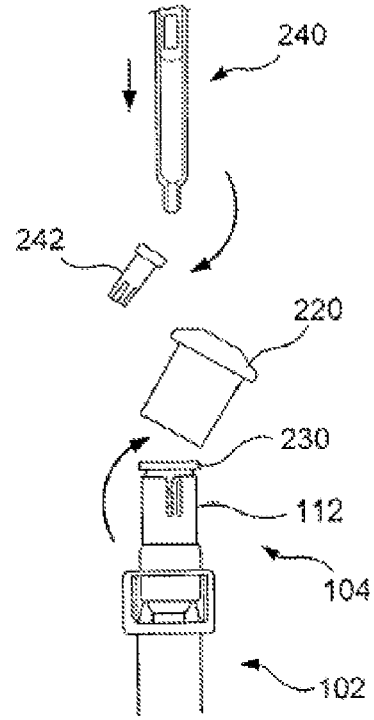
Figure 16:
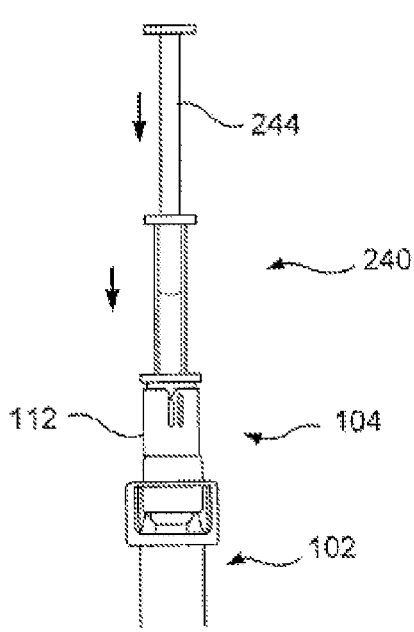
Figure 17:
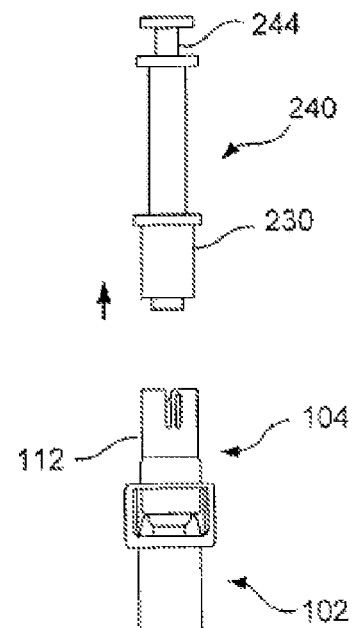

FIGS. 14-17 illustrate a process for reconstituting medicament using a syringe 240. In FIG. 14 each of the vial 102, the liquid-transfer adapter 104 and the syringe 240 are shown as initially being separate from each other. The liquid-transfer adapter 104 may be moved downward to engage the vial 102. In FIG. 15, the cap 220 is removed from the liquid-transfer adapter 104 and a cap 242 is removed from the syringe 240. The syringe 240 engages the liquid-transfer adapter 104 by entering the injector engaging end 112 of the adapter. Once the syringe 240 and the liquid-transfer adapter 104 are joined together, a plunger 244 of the syringe 240 may be depressed to insert liquid into the vial, as shown in FIG. 16. Once the liquid from the syringe has been inserted into the vial 102, the syringe 240 will be removed from the liquid-transfer adapter 104. As illustrated in FIG. 17, when the syringe is withdrawn from the injector engaging end 112 of the liquid-transfer adapter 104, the insert 230 will be extracted from the liquid-transfer as well.

Figure 18:
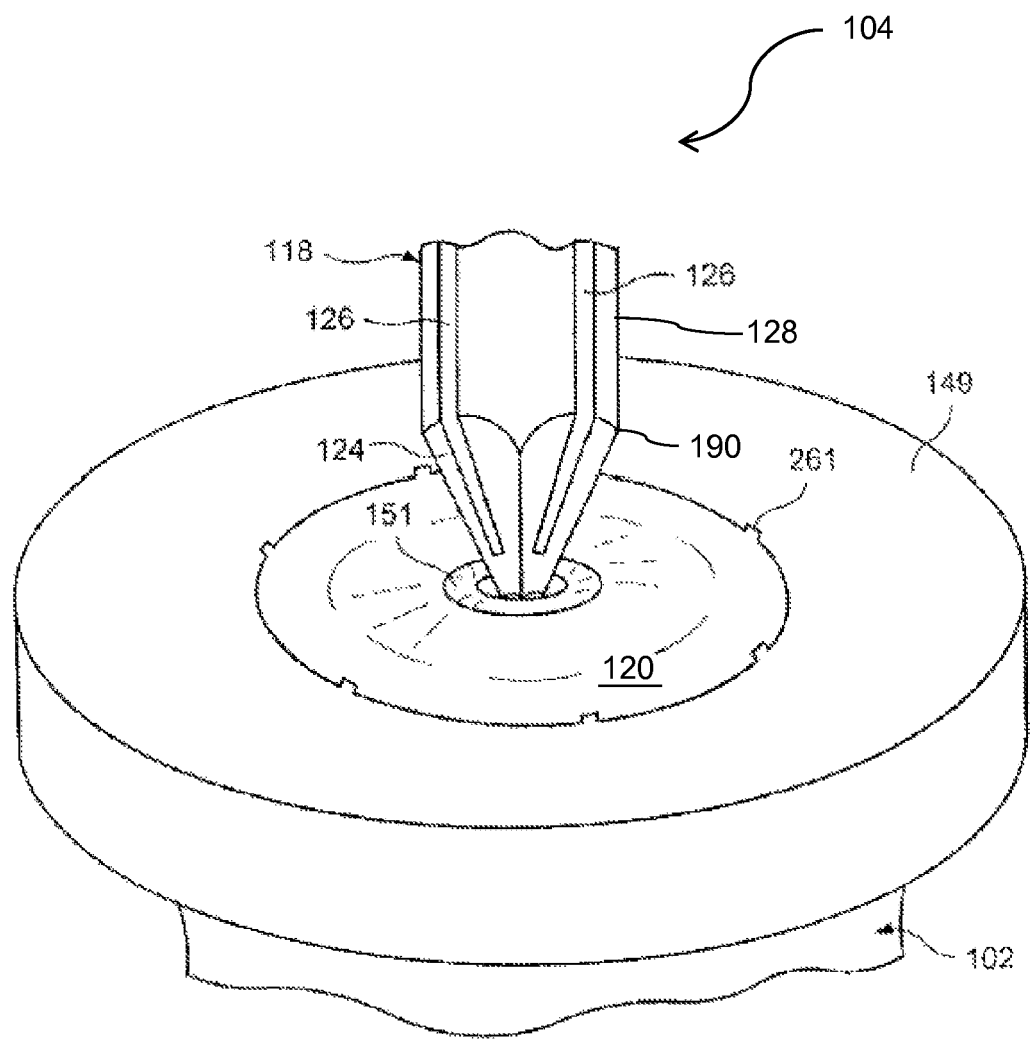
FIG. 18 is a perspective view of an embodiment of a spike penetrating a septum of a vial.
Figure 19:
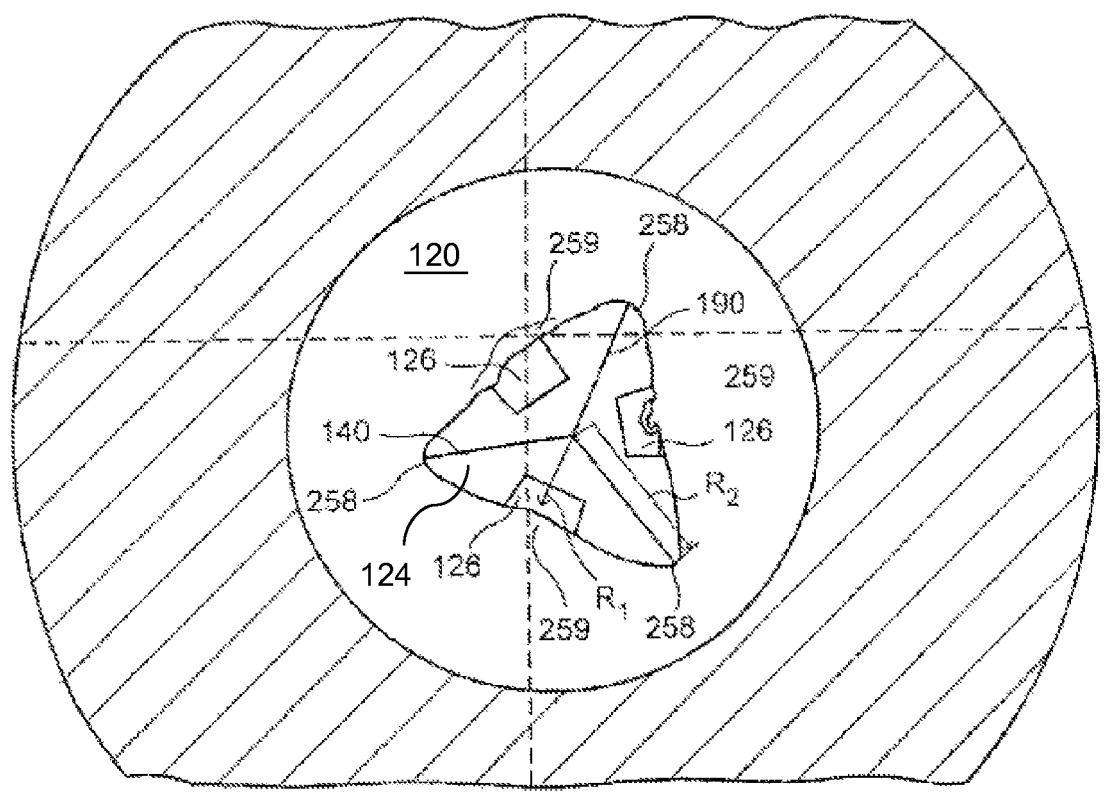
FIGS. 19 and 20 are axial views of the spike of FIG. 18 partially and completely, respectively, penetrating through the septum of a vial.
Figure 20:
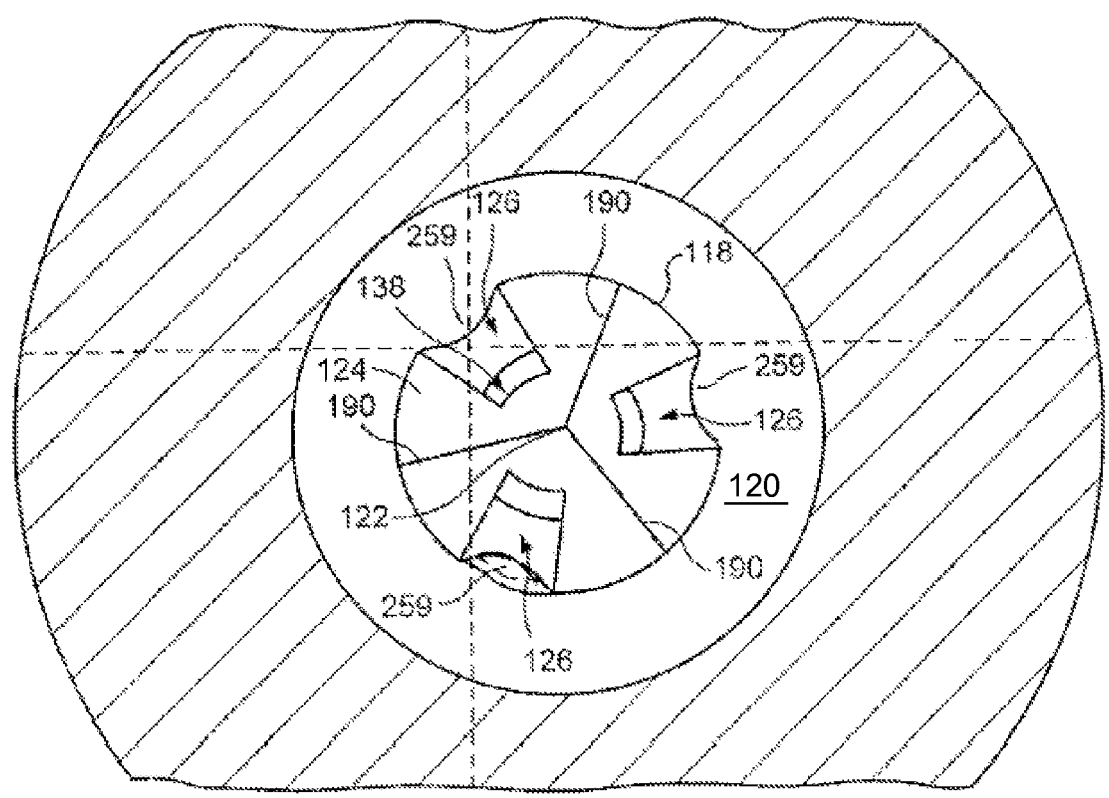

FIGS. 18-20 are images of the spike 118 penetrating the rubber stopper 120 of the vial 102, for example when the liquid-transfer adapter 104 is engaging the vial. In particular, FIG. 18 shows the spike 118 from outside the vial 102. The multiple facets 124 may be seen as having channel openings 126 that extend on the sidewall 128 of the shaft 129 of the spike 118. Additionally, the metal cap 149 may be seen. The tab of the metal cap has been removed to allow the spike access to the stopper 120 and remnants 261 of where the tab was connected to the metal cap 149 remain. The protrusion 151 of the stopper 120 is also shown and serves as a target for the spike 118. The edges 190 at the junction between facets 124 serve as cutting edges as the spike 118 punctures the stopper 120.

FIG. 19 shows a view from within the vial as the spike 118 is pushed through the stopper 120. In some embodiments, tearing of the stopper 120 may occur upon insertion of the spike 118. In one embodiment, the edges 190 are sufficiently sharp to provide cutting through the elastomeric stopper 120 to facilitate penetration of the spike 118 therein. As the edges 190 extend radially further than the facet's 124 surfaces the pressure from the stopper 120 is concentrated at the edges 190. More specifically, stress concentrations from cutting, stretching, and/or tearing of the stopper 120 are localized away from the openings 126 and instead are focused at the points 258 where the edges 190 are contacting the stopper. Thus, the channel openings 126 generally do not provide edges or points for cutting the stopper. This can help avoid coring of the stopper and minimize intrusion of the stopper 120 into the openings 126. In one embodiment, the stopper 120 material will be pulled away from the channels 126 by the edges 190, and the stopper material that expands into the openings is minimized, such as at 259.

FIG. 20 shows the spike 118 fully inserted into the vial 102. As may be seen, the edges 190 are cleared from the stopper 120 and the channel openings 126 are exposed. Although not shown here, as the spike 118 is pushed through the stopper 120, the stopper 120 is deflected slighted into the vial 102. As such, in one embodiment, the distal end of the channel openings 126 are either flush with the stopper 120 or remain within the stopper 120 so that substantially all of the liquid within the vial may be extracted into an injector, as discussed above.

Figure 21:
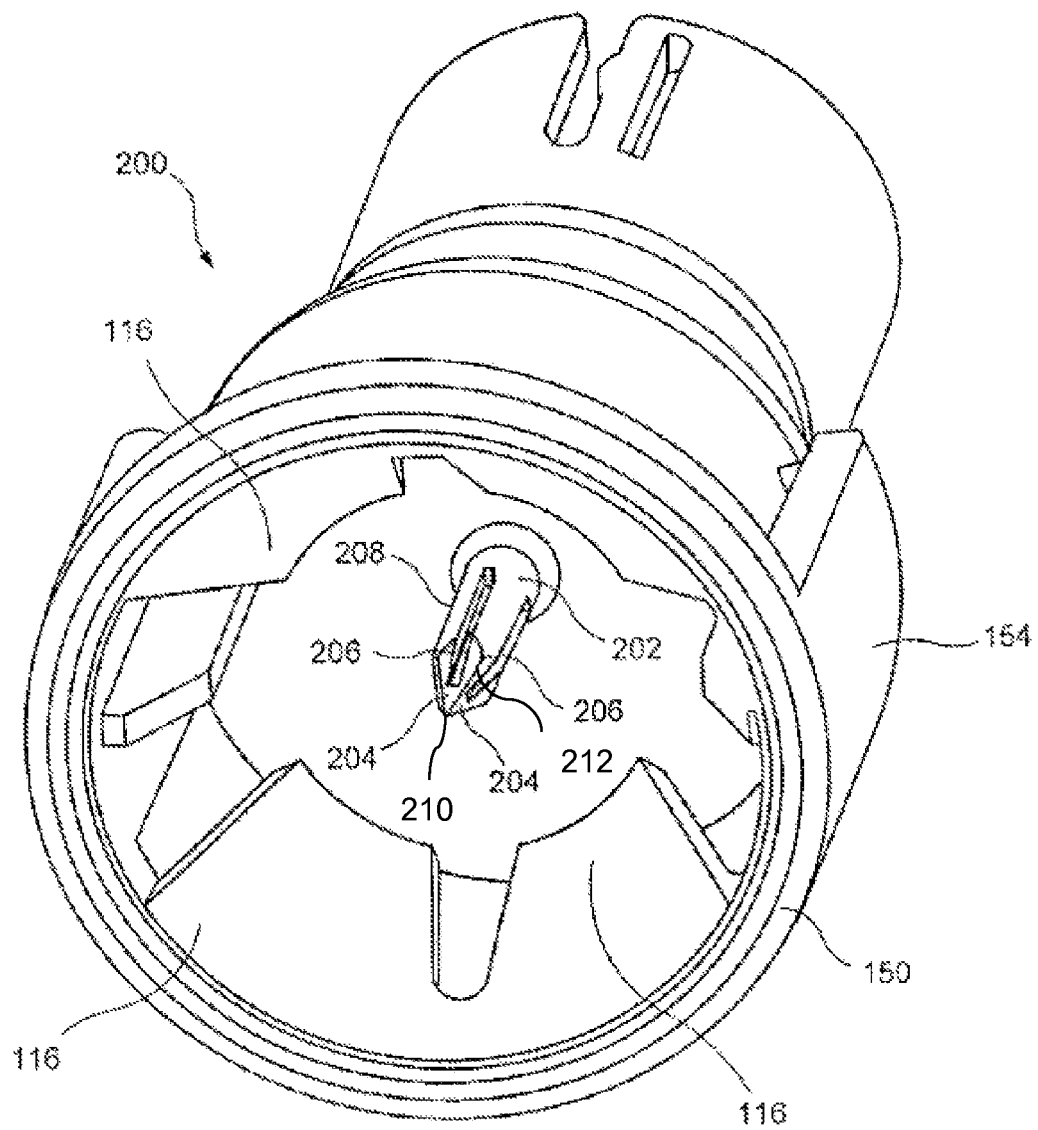
FIG. 21 illustrates a spike having four facets in accordance with and alternative embodiment.

FIG. 21 is a perspective view of another embodiment of a liquid-transfer adapter 200, which has a spike 202 with four facets 204. Each facet 204 may be similarly or differently sized, and in one embodiment has a channel opening 206 that extends from within the face of the facet and onto the sidewall 208 of the spike 202. The channel opening 206 is in communication with a channel (not shown) within the spike 202 to provide liquid communication between two ends of the liquid-transfer 200.

The facets 204 meet at a tip 210 and each facet joins with adjacent facets to form edges 212 (referred to in other embodiments as edge 190). The tip 210 is axially centered with respect to the spike 202. The edges 212 at the junction of the facets 204 may be used to cut through a rubber septum or stopper of a vial. Hence, the edges 212 are cutting edges. Furthermore, the channel openings 206 (referred to in other embodiments as channels 126) are positioned between the edges 212 but do not interfere or disrupt the edges. As such, the edges 212 are disposed more radially outward than the interior portions of the facets 204 where the channel openings 206 are positioned. The outward position of the edges 212 localizes the strain concentrations of the septum thereon and away from the channel openings 206 as the spike 202 penetrates it.

All of the references specifically identified in the detailed description section of the present application are expressly incorporated herein in their entirety by reference thereto. The term "about," as used herein, should generally be understood to refer to both the corresponding number and a range of numbers. Moreover, all numerical ranges herein should be understood to include each whole integer within the range, and other embodiments can have other dimensions. Accordingly, the specific embodiments described herein should be understood as examples and not limiting the scope thereof While illustrative embodiments of the disclosure are disclosed herein, it will be appreciated that numerous modifications and other embodiments may be devised by those skilled in the art. For example, the features tier the various embodiments can be used in other embodiments. Therefore, it will be understood that the appended claims are intended to cover all such modifications and embodiments that come within the spirit and scope of the present disclosure. The content of each and every reference cited above is hereby incorporated by reference in its entirety as if fully set forth herein.

What is claimed is:

1. A liquid-transfer adapter operatively interposable between an injector and a vial, comprising:
    an injector engaging portion configured for fluidly coupling to an injector; and
    a vial coupling configured to engage a lip of a vial, the vial coupling including a spike that has a spike axis and a tip portion configured for piercing a septum of the vial, the tip portion including at least three facets that meet each other at a plurality of edges, at least one of the plurality of edges being sloped with respect to the spike axis, the spike defining a channel extending therethrough in fluid communication with the injector engaging portion and including a channel opening defined in each of the at least three facets and disposed without interrupting the edges; and
    wherein the vial coupling includes a collar configured to act as a guide for the vial such that the spike pierces the septum of the vial without piercing a sidewall of the septum as the vial is moved into engagement with the vial coupling.

2. The liquid-transfer adapter of claim 1, wherein the edges comprise junctions between the facets.

3. The liquid-transfer adapter of claim 1, wherein the edges comprise cutting surfaces configured for cutting the septum as the spike is pushed therethrough.

4. The liquid-transfer adapter of claim 1 further comprising a seal disposed at the injector engaging portion configured for mating with the injector or a removable insert for maintaining liquid within the channel and injector.

5. The liquid-transfer adapter of claim 1, further comprising a vial engaging member associated with the vial coupling configured for engaging the liquid-transfer to the vial with the spike inserted therein.

6. The liquid-transfer adapter of claim 5, wherein the vial engaging member comprises reflexed fingers arranged around the spike and extending theretowards for snapping to and retaining the liquid-transfer adapter engaged to the vial.

7. The liquid-transfer adapter of claim 6, wherein the reflexed fingers are positioned between the collar and an attachment point where the spike is coupled to the vial coupling member.

8. The liquid-transfer adapter of claim 1, wherein the channel openings are spaced circumferentially from each of the edges.

9. The liquid-transfer adapter of claim 1, wherein lateral edges of the channel openings are disposed radially inward compared to the edges.

10. The liquid-transfer adapter of claim 1, wherein lateral edges of the channel openings are disposed radially inward relative to the edges at any axial position.

11. The liquid-transfer adapter of claim 1, wherein lateral edges of the channel openings are spaced from each of the edges sufficiently to prevent intrusion of the septum into the channel openings when the spike is pierced through the septum.

12. The liquid-transfer adapter of claim 1, wherein the channel openings are substantially centered circumferentially on the facets.

13. The liquid-transfer adapter of claim 1, wherein the injector engaging portion comprises dimensions suitable for coupling with a needle free injector or a removable insert.

14. The liquid-transfer adapter of claim 13, wherein a removable insert is removably coupled within the injector engaging portion for selectively configuring the injector engaging portion for engaging variously sized injectors.

15. The liquid-transfer adapter of claim 14, wherein the removable insert comprises dimensions suitable for coupling with a syringe having a first width, and with the insert removed, the injector engaging portion is configured for coupling to a jet injector having a second width that is larger than the first width.

16. The liquid-transfer adapter of claim 1, wherein:
    the spike comprises a shaft extending from the tip towards the injector engaging portion; and
    the opening extends onto the shaft for maximizing thereby allowing fluid extraction from the vial with the vial in an inverted position.

17. The liquid-transfer adapter of claim 1, wherein the edges meet at a point that is substantially axially centered.

18. The liquid-transfer adapter of claim 1, wherein the facets are substantially flat bevels.

19. The liquid-transfer adapter of claim 1, wherein the collar is configured to align the spike perpendicularly to a top surface of the septum prior to the spike contacting the septum.

20. The liquid-transfer adapter of claim 1, wherein a height of the collar is at least about 0.50 inches.

21. The liquid-transfer adapter of claim 1, wherein the collar surrounds at least a portion of the vial when the vial is engaged with the vial coupling.

* * * * *